US010262507B2

(12) United States Patent
Sloo et al.

(10) Patent No.: US 10,262,507 B2
(45) Date of Patent: Apr. 16, 2019

(54) SMART-HOME HAZARD DETECTION SYSTEM PROVIDING CONTEXT-BASED USER NOTIFICATIONS

(71) Applicant: Google LLC, Mountain View, CA (US)

(72) Inventors: David Sloo, Menlo Park, CA (US); Jesse W. Boettcher, San Jose, CA (US); Maxime Veron, San Jose, CA (US); Sophie Le Guen, Burlingame, CA (US)

(73) Assignee: Google LLC, Mountain View, CA (US)

( * ) Notice: Subject to any disclaimer, the term of this patent is extended or adjusted under 35 U.S.C. 154(b) by 709 days.

(21) Appl. No.: 14/508,485

(22) Filed: Oct. 7, 2014

(65) Prior Publication Data

US 2015/0097683 A1    Apr. 9, 2015

Related U.S. Application Data

(60) Provisional application No. 61/887,963, filed on Oct. 7, 2013, provisional application No. 61/887,969, filed on Oct. 7, 2013.

(51) Int. Cl.
*G08B 5/36* (2006.01)
*G08B 17/10* (2006.01)
(Continued)

(52) U.S. Cl.
CPC ............ *G08B 5/36* (2013.01); *F24F 11/30* (2018.01); *F24F 11/33* (2018.01); *F24F 11/34* (2018.01);
(Continued)

(58) Field of Classification Search
CPC ...... G08B 29/02; G08B 29/04; G08B 25/008; G08B 25/08; G08B 21/14; G08B 21/18;
(Continued)

(56) References Cited

U.S. PATENT DOCUMENTS

| 4,254,414 A | 3/1981 | Street et al. |
| 4,313,110 A | 1/1982 | Subulak et al. |

(Continued)

OTHER PUBLICATIONS

International Search Report and Written Opinion dated Apr. 21, 2016, for International Patent Application No. PCT/US2014/059538, 13 pages.

(Continued)

*Primary Examiner* — Mirza F Alam
(74) *Attorney, Agent, or Firm* — Kilpatrick Townsend & Stockton LLP

(57) ABSTRACT

System for customizing hazard notifications based on user activity includes a hazard detector and a computer server system communicatively coupled to the hazard detector. The hazard detector detects a hazard level that is greater than a threshold setting, the hazard level indicating an amount of smoke or carbon monoxide present at the hazard detector. The hazard detector generates hazard data indicating the detection of the hazard level and transmits the hazard data to the computer server system. The computer server system associates a location with the hazard detector. Activity data indicating a user location is received at the computer server system and the hazard data is received at the computer server system. The computer server system generates a notification based on the hazard location and the user location in response to receiving the hazard data.

20 Claims, 12 Drawing Sheets

(51) Int. Cl.

| | | |
|---|---|---|
| F24F 11/30 | (2018.01) | |
| G01N 27/02 | (2006.01) | |
| G01N 27/12 | (2006.01) | |
| G01N 33/00 | (2006.01) | |
| G08B 25/00 | (2006.01) | |
| G08B 21/18 | (2006.01) | |
| G08B 29/18 | (2006.01) | |
| G08B 3/10 | (2006.01) | |
| G08B 21/14 | (2006.01) | |
| H04L 12/28 | (2006.01) | |
| G08B 5/22 | (2006.01) | |
| G08B 21/12 | (2006.01) | |
| G08B 25/01 | (2006.01) | |
| G08B 29/02 | (2006.01) | |
| G08B 29/04 | (2006.01) | |
| G08B 29/26 | (2006.01) | |
| G08B 17/117 | (2006.01) | |
| G08B 29/22 | (2006.01) | |
| H04L 29/08 | (2006.01) | |
| F24F 11/33 | (2018.01) | |
| G01J 1/42 | (2006.01) | |
| G01V 8/10 | (2006.01) | |
| H05B 33/08 | (2006.01) | |
| H05B 37/02 | (2006.01) | |
| G06T 7/70 | (2017.01) | |
| G06K 9/00 | (2006.01) | |
| H04M 1/725 | (2006.01) | |
| H04N 7/18 | (2006.01) | |
| F24F 11/34 | (2018.01) | |
| G08B 25/08 | (2006.01) | |
| F24F 120/10 | (2018.01) | |
| F24F 11/46 | (2018.01) | |
| F24F 11/58 | (2018.01) | |
| G08B 19/00 | (2006.01) | |
| F24F 11/75 | (2018.01) | |
| F24F 11/89 | (2018.01) | |
| F24F 11/70 | (2018.01) | |

(52) U.S. Cl.
CPC ............ *G01J 1/4204* (2013.01); *G01N 27/02* (2013.01); *G01N 27/121* (2013.01); *G01N 33/004* (2013.01); *G01N 33/0031* (2013.01); *G01V 8/10* (2013.01); *G06K 9/00744* (2013.01); *G06T 7/70* (2017.01); *G08B 3/10* (2013.01); *G08B 5/22* (2013.01); *G08B 17/10* (2013.01); *G08B 17/117* (2013.01); *G08B 21/12* (2013.01); *G08B 21/14* (2013.01); *G08B 21/18* (2013.01); *G08B 21/182* (2013.01); *G08B 25/002* (2013.01); *G08B 25/008* (2013.01); *G08B 25/012* (2013.01); *G08B 29/02* (2013.01); *G08B 29/04* (2013.01); *G08B 29/185* (2013.01); *G08B 29/22* (2013.01); *G08B 29/26* (2013.01); *H04L 12/282* (2013.01); *H04L 12/2803* (2013.01); *H04L 12/2809* (2013.01); *H04L 12/2818* (2013.01); *H04L 67/10* (2013.01); *H04L 67/24* (2013.01); *H04M 1/72561* (2013.01); *H04N 7/183* (2013.01); *H05B 33/0854* (2013.01); *H05B 33/0872* (2013.01); *H05B 37/0218* (2013.01); *H05B 37/0272* (2013.01); *F24F 11/46* (2018.01); *F24F 11/58* (2018.01); *F24F 11/70* (2018.01); *F24F 11/75* (2018.01); *F24F 11/89* (2018.01); *F24F 2120/10* (2018.01); *G08B 19/005* (2013.01); *G08B 25/08* (2013.01); *H04L 67/025* (2013.01); *Y02A 50/243* (2018.01)

(58) Field of Classification Search
CPC .... G08B 21/182; G08B 17/117; G08B 21/12; G08B 17/10; G08B 17/107; G01N 33/0031; G01N 33/004
USPC .......................................................... 340/517
See application file for complete search history.

(56) References Cited

U.S. PATENT DOCUMENTS

| | | | |
|---|---|---|---|
| 4,390,869 A | 6/1983 | Christen et al. | |
| 6,624,750 B1 | 9/2003 | Marman et al. | |
| 7,649,472 B1* | 1/2010 | Paterno | F21V 33/0076 307/116 |
| 8,172,154 B1* | 5/2012 | Figley | F24F 11/30 236/44 A |
| 2004/0140892 A1* | 7/2004 | Hanood | B60R 25/1004 340/511 |
| 2007/0255522 A1 | 11/2007 | Gordon et al. | |
| 2010/0195810 A1 | 8/2010 | Mota et al. | |
| 2010/0325074 A1 | 12/2010 | Ng et al. | |
| 2012/0126975 A1* | 5/2012 | Gonzales | G08B 29/20 340/540 |
| 2012/0229285 A1 | 9/2012 | Rauworth et al. | |
| 2014/0085093 A1* | 3/2014 | Mittleman | H04L 12/282 340/628 |
| 2015/0015401 A1* | 1/2015 | Wedig | G08B 17/10 340/577 |
| 2015/0077737 A1* | 3/2015 | Belinsky | G01N 15/0211 356/51 |

OTHER PUBLICATIONS

International Search Report and Written Opinion dated Apr. 21, 2016, for International Patent Application No. PCT/US2014/059526, 9 pages.

International Office Action dated Dec. 24, 2014 for International Patent Application PCT/US2014/059538 filed on Oct. 7, 2014, all pages.

ISR/WO mailed on Feb. 26, 2015 for International Patent Application PCT/US2014/059538 filed on Oct. 7, 2014, all pages.

* cited by examiner

SMART-HOME HAZARD DETECTION SYSTEM PROVIDING CONTEXT-BASED USER NOTIFICATIONS

CROSS-REFERENCES TO RELATED APPLICATIONS

This application claims the benefit of U.S. Provisional Patent Application No. 61/887,963, filed Oct. 7, 2013, entitled "HAZARD DETECTION IN A SMART-SENSORED HOME," and U.S. Provisional Patent Application No. 61/887,969, filed Oct. 7, 2013, entitled "USER-FRIENDLY DETECTION UNIT," the entire disclosures of which are hereby incorporated by reference for all purposes.

BACKGROUND

1. The Field of the Invention

The present invention generally relates to hazard detection. More specifically, the present invention relates to network connected hazard detection units that provide customized notifications.

2. The Relevant Technology

Hazard detectors use a variety of sensors to detect substances in the air that are harmful or indicate the development of a hazardous situation. For example, carbon monoxide (CO) and radon gas are substances that can be harmful to humans and animals if exposed to high amounts. However, these substances are difficult to detect with the human senses because they are colorless, odorless, and tasteless. A hazard detector can detect the presence of these substances and prevent the harmful effects of exposure by alarming a user. In other instances, a substance such as smoke, while not necessarily harmful in and of itself, can indicate the development of a hazardous situation, such as fire. An early alarm of the presence of such a substance can prevent the hazardous situation from developing or minimize the harmful effects of the situation.

Interconnected hazard detectors are detectors that are connected to a network, enabling communication between the detectors or with a central control unit. This provides several advantages over standalone detectors, including the ability to activate multiple alarms when a single detector is triggered.

BRIEF SUMMARY

In one embodiment, a system for customizing hazard notifications based on user activity is presented. The system includes a plurality of motion detecting modules, a hazard detector, and a computer server system. The computer server system is communicatively coupled to the plurality of motion detecting modules and the hazard detector.

Each motion detecting module is configured to detect activity, generate activity data indicating the detection of the activity, and transmit the activity data to a computer server system.

The hazard detector is configured to detect a hazard level that is greater than a threshold setting. The hazard level indicates an amount of smoke or carbon monoxide (CO) that is present at the hazard detector. The hazard detector is further configured to generate hazard data indicating the detection of the hazard level, and transmit the hazard data to the computer server system.

The computer server system is configured to associate an activity location with each of the plurality of motion detecting modules, the activity location indicating a location of an associated motion detecting module within an enclosure. The computer server system receives a first activity data, and identifies a first motion detecting module that transmitted the first activity data. The computer server system is further configured to determine a first activity location associated with the first motion detecting module. The computer server system receives the hazard data, and generates a notification in response to receiving the hazard data. The notification is generated based on the first activity location.

In another embodiment, a method is presented for customizing hazard notifications based on user activity. The method includes storing a threshold setting and a volume setting for a hazard detector. Activity data indicating an activity of a user is received, and the threshold setting or the volume setting of the hazard detector is adjusted based on the activity data. A hazard level that is greater than the threshold setting is detected, the hazard level indicating an amount of smoke or carbon monoxide (CO) present at the hazard detector. An audible notification is generated in response to detecting the hazard level, the audible notification having a volume corresponding to the volume setting.

In a further embodiment, a system is presented for customizing hazard notifications based on user activity. The system includes a hazard detector and a computer server system that is communicatively coupled to the hazard detector.

The hazard detector is configured to detect a hazard level that is greater than a threshold setting, the hazard level indicating an amount of smoke or carbon monoxide (CO) present at the hazard detector. The hazard detector is further configured to generate hazard data indicating the detection of the hazard level, and transmit the hazard data to the computer server system.

The computer server system is configured to associate a hazard location with the hazard detector, the hazard location indicating a location of the hazard detector. The computer server system receives activity data indicating a user location of a user, and receives the hazard data. The computer server system generates a notification in response to receiving the hazard data, the notification being generated based on the hazard location and the user location.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

Figure 1:
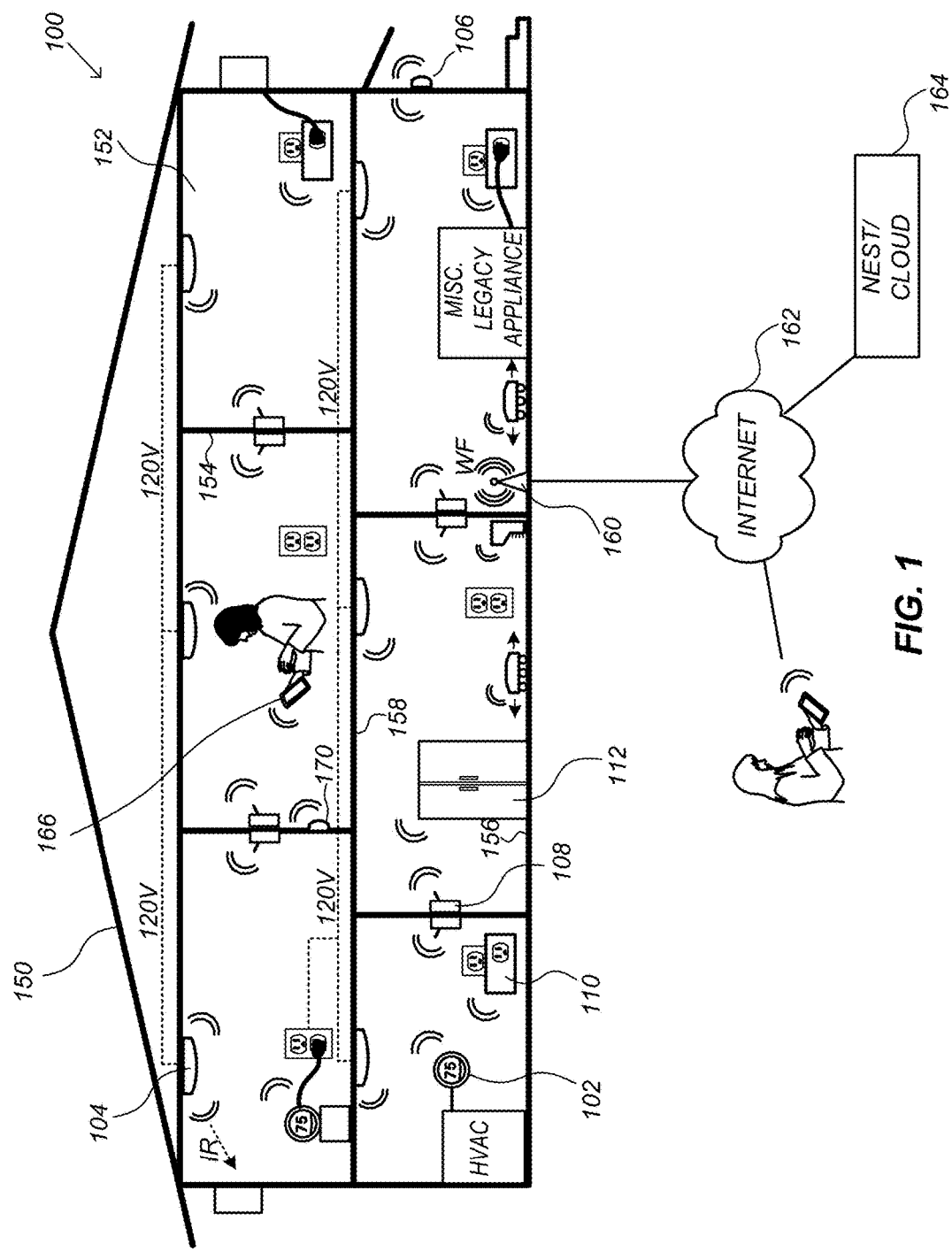
FIG. 1 is an example of a smart-home environment within which one embodiment of a system for generating customized hazard notifications based on user activity can be implemented.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Interconnected hazard detectors are typically used in large buildings and complexes. In these environments, the hazard detectors are connected to a central control unit. Some jurisdictions also require interconnected hazard detectors at home, in which case the hazard detectors are connected to each other rather than a central control unit. The networking of hazard detectors in an interconnected system enables more effective automated responses. For example, when a hazard detector is triggered, a fire suppression system (e.g., a sprinkler system) at or near the triggered detector can be activated. In other instances, all of the connected detectors can activate an alarm when a single detector is triggered, or an alarm system can be activated to notify an entire building or complex of the hazardous situation.

However, although interconnected hazard systems provide more effective responses compared to standalone hazard detectors, there are still situations where even interconnected systems are not effective. For example, if no one is home when a hazardous situation develops, activating an alarm, or even multiple alarms, inside the home will not be an effective response for preventing property damage. In another example, a user can become disoriented during a hazardous situation (e.g., smoke can obscure the user's vision or the user is in an unfamiliar surrounding), in which case alarming the user of the situation will not be a sufficient response for preventing harm to the user. In yet another example, the activities of the user can render the user more susceptible to harmful substances. A user performing heavy exercise can be significantly impaired by even low amounts of carbon monoxide (CO). Thus, by the time an alarm is activated, the user can have already experienced the harmful effects of exposure.

The embodiments of the invention described herein below overcome the disadvantages of the prior art by providing methods and systems for generating customized hazard notifications based on user activity. User activity data can be collected from different sources, such as motion detectors or a mobile device of the user. In some embodiments, the user activity data indicates a location of the user. A customized notification is generated based on the activity data. In one embodiment, the system also takes into account the location of the triggered hazard detector when generating the customized notification. In another embodiment, the customized notification is generated by adjusting the threshold or volume settings of the hazard detector.

FIG. 1 is an example of a smart-home environment 100 within which one embodiment of a system for generating customized hazard notifications based on user activity can be implemented. The depicted smart-home environment 100 includes an enclosure 150, which can be, e.g., a house, office building, hotel, retail store, garage, or mobile home. The system can also be implemented in a smart-home environment 100 that does not include an entire enclosure 150, such as an apartment, condominium, or office space.

The depicted enclosure 150 includes a plurality of rooms 152, separated at least partly from each other via walls 154. The walls 154 can include interior walls or exterior walls. Each room can further include a floor 156 and a ceiling 158. Devices can be mounted on, integrated with and/or supported by a wall 154, floor 156 or ceiling 158. Further, the smart home environment can include devices outside of the actual enclosure 150, such as a pool heater or irrigation system.

The smart-home environment 100 includes a plurality of intelligent, multi-sensing, network-connected devices (hereinafter referred to as "the smart devices") that can integrate seamlessly with each other and with a computer server system 164, such as a cloud-computing system. The smart devices can include smart thermostats 102, smart hazard detectors 104, smart entryway devices 106 (e.g., doorbells or intercoms), smart wall switches 108, smart wall plug interfaces 110, and smart appliances 112, such as refrigerators, stoves and/or ovens, televisions, washers, dryers, lights, stereos, intercom systems, garage-door openers, floor fans, ceiling fans, wall air conditioners, pool heaters, irrigation systems, security systems, and so forth.

Any of the smart devices in the smart-home environment can include sensors that detect user activity. For example, smart appliances 112 can include sensors that detect when they are being used. Additionally, a motion or occupancy sensor, such as an ultrasonic, passive infrared (PIR), or optical sensor, can be included in any of the smart devices to detect user activity and movement. Some smart devices will also have sensors specific to the device. For example, a smart light can include an ambient light sensor, such as a photoresistor or a single-pixel sensor that measures light in the room. Smart hazard detectors 104 can include smoke/fire/heat sensors, carbon monoxide/dioxide sensors, radon gas detectors, ambient light sensors, temperature sensors, humidity sensors, and the like. Any smart device can also include a processor for processing data from the sensors or other devices.

User activity data can also be generated by sensors that detect the user's mobile device. For example, when the mobile device transmits data wirelessly, e.g., using WiFi, Bluetooth, or NFC, the data includes a unique identifier for the mobile device, e.g., a media access control address (MAC address). A smart device that communicates with the mobile device can use the unique identifier to identify the mobile device or the user of the mobile device, and generate activity data indicating that the user is near the smart device. Passive radio-frequency identification (RFID) tags can also be included in the user's possessions, e.g., wallets, bracelets, wristbands, mobile devices, or collars. Thus, smart devices with RFID readers can generate activity data indicating the location of the user when the RFID tags are detected.

Each smart device is also equipped with communications ports or transceivers for communicating data with other smart devices. In one embodiment, the devices establish a mesh network for communication between devices. In another embodiment, the devices can connect, via a router or gateway 160, to a private network or the internet 162, including any computer server system 164 and computing device that is connected to the same network. Data can be transferred via any wireless (e.g., Wi-Fi, ZigBee, 6LoWPAN, etc.) or wired (CAT6 Ethernet, HomePlug, etc.) protocols.

By virtue of network connectivity, one or more of the smart devices can further allow a user to interact with the device even if the user is not proximate to the device. For example, a user can communicate with a device using a computer (e.g., a desktop computer) or mobile device (e.g., a smartphone, laptop computer, or tablet) 166. A webpage or native mobile app can be configured to receive input from the user and control the device based on the input. The webpage or mobile app can also present information about the device's operation to the user. For example, the user can view the status of a smart hazard detector or a history of notifications generated by the smart hazard detector. The user can be in the enclosure during this remote communication or outside the enclosure.

Figure 2:
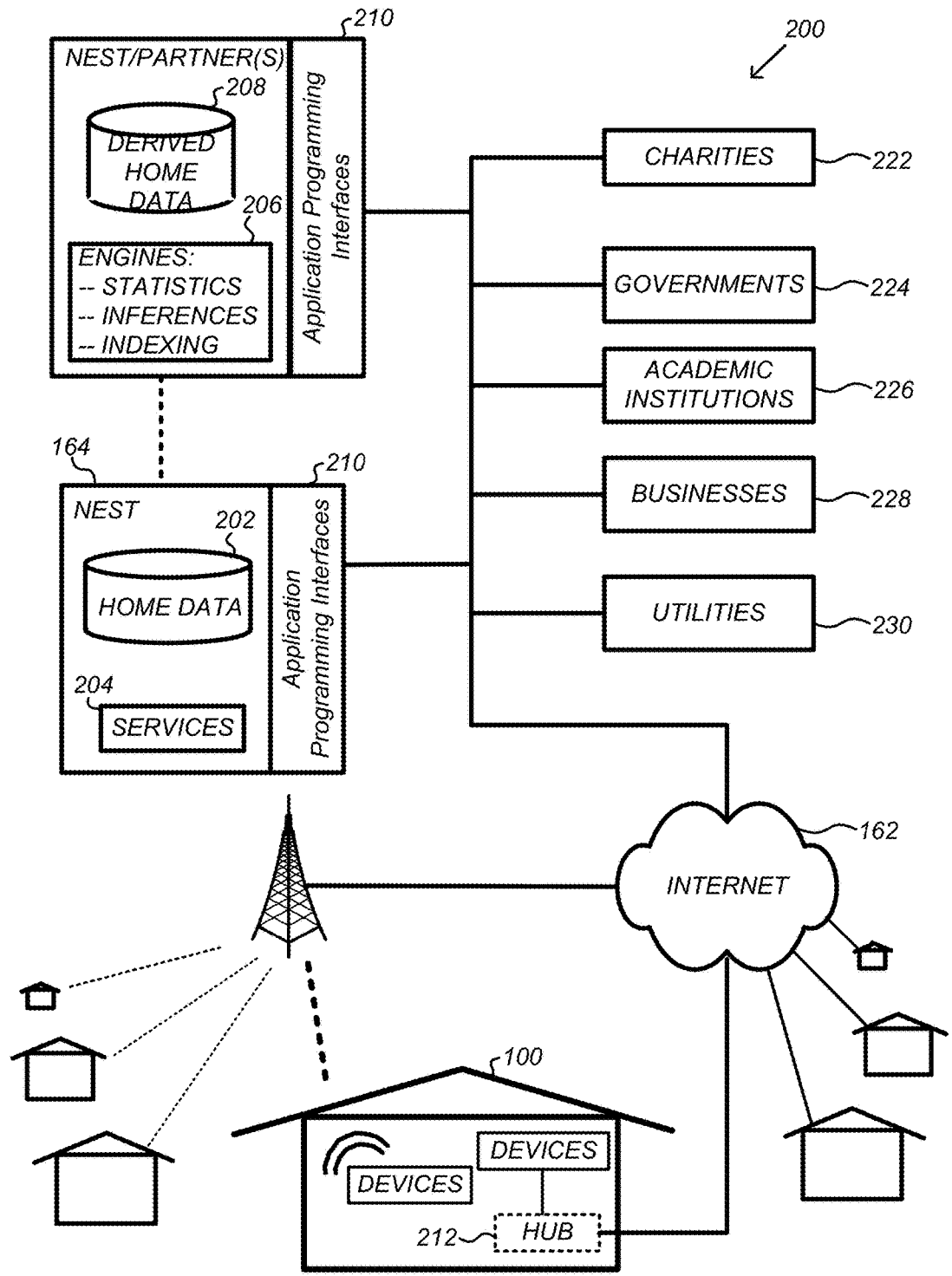
FIG. 2 is a network-level view of one embodiment of a system for generating customized hazard notifications based on user activity.

FIG. 2 is a network-level view of one embodiment of a system 200 for generating customized hazard notifications based on user activity. System 200 includes computer server system 164. Smart devices can communicate with the computer server system 164 via a private network or the internet 162. Smart devices can transmit home data 202, including user data and user activity data, to computer server system 164 for processing or storage. More specifically, home data 202 can include power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, etc.

The computer server system 164 can further provide one or more services 204. The services 204 can include customized hazard notifications, software updates, customer support, sensor data collection/logging, remote access, remote or distributed control, or use suggestions (e.g., based on collected home data 202 to improve performance, reduce utility cost, etc.). To facilitate these services, users can register the smart devices in their home or enclosure with the computer server system 164. Computer server system 164 can associate the smart devices with an account during the registration process. The account can be user specific or specific to a home or enclosure that includes multiple users, and a unique identification of each smart device can be stored in the account. In one embodiment, the user's mobile device or other computing device can also be associated with the account during registration. In another embodiment, one or more username and password is associated with the account during registration. The user can then use the username and password to login on the mobile or computing device, and computer server system 164 can use the account to authorize the user's mobile or computing device for the services 204. Data associated with the services 204, such as account data, can be stored at the computer server system 164.

System 200 includes a processing engine 206, which can be concentrated at a single server or distributed among several different computing entities without limitation. A single server can also include multiple engines for performing different processing tasks. The processing engine 206 can receive data from smart devices, index and store the data, or process the data to generate customized notifications or statistics. The processed data can be stored as derived home data 208. Results of the processing can be transmitted back to the device that provided the home data, to other devices, to a server providing a webpage to a user of the device, or to other non-device entities. For example, customized hazard notifications can be generated by the processing engine 206 and transmitted to a user device via the Internet 162. In this manner, the processing engine 206 can be configured and programmed to derive a variety of useful information from the home data 202.

In some embodiments, to encourage innovation and research and to increase products and services available to users, system 200 provides application programming interfaces (APIs) 210 to third parties, such as charities 222, governmental entities 224 (e.g., emergency response units such as a fire department or police department, the Food and Drug Administration, or the Environmental Protection Agency), academic institutions 226 (e.g., university researchers), businesses 228 (e.g., security or fire monitoring service providers, social network providers, device warranty or equipment service providers, or providers of targeted advertisements based on home data), utility companies 230, and other third parties. The APIs 210 permit third-party systems to communicate with the computer server system 164, providing access to the services 204, the processing engine 206, the home data 202, and the derived home data 208. This allows third-party applications to submit specific data processing tasks to the computer server system 164 and receive dynamic updates to the home data 202 and the derived home data 208. For example, a fire department or fire monitoring service provider can develop applications using the APIs 210 to provide emergency response services to users.

In other embodiments, the services 204 can utilize third-party APIs to communicate with third-party applications. For example, if a smart hazard detector is triggered, a customized notification can be transmitted to an emergency response system, such as one provided by a fire department, using an API of the emergency response system. Third-party APIs can also be used to collect user data and user activity data from third-parties. For example, an API of a social network provider can be utilized to gather user activity data for a user.

Figure 3:
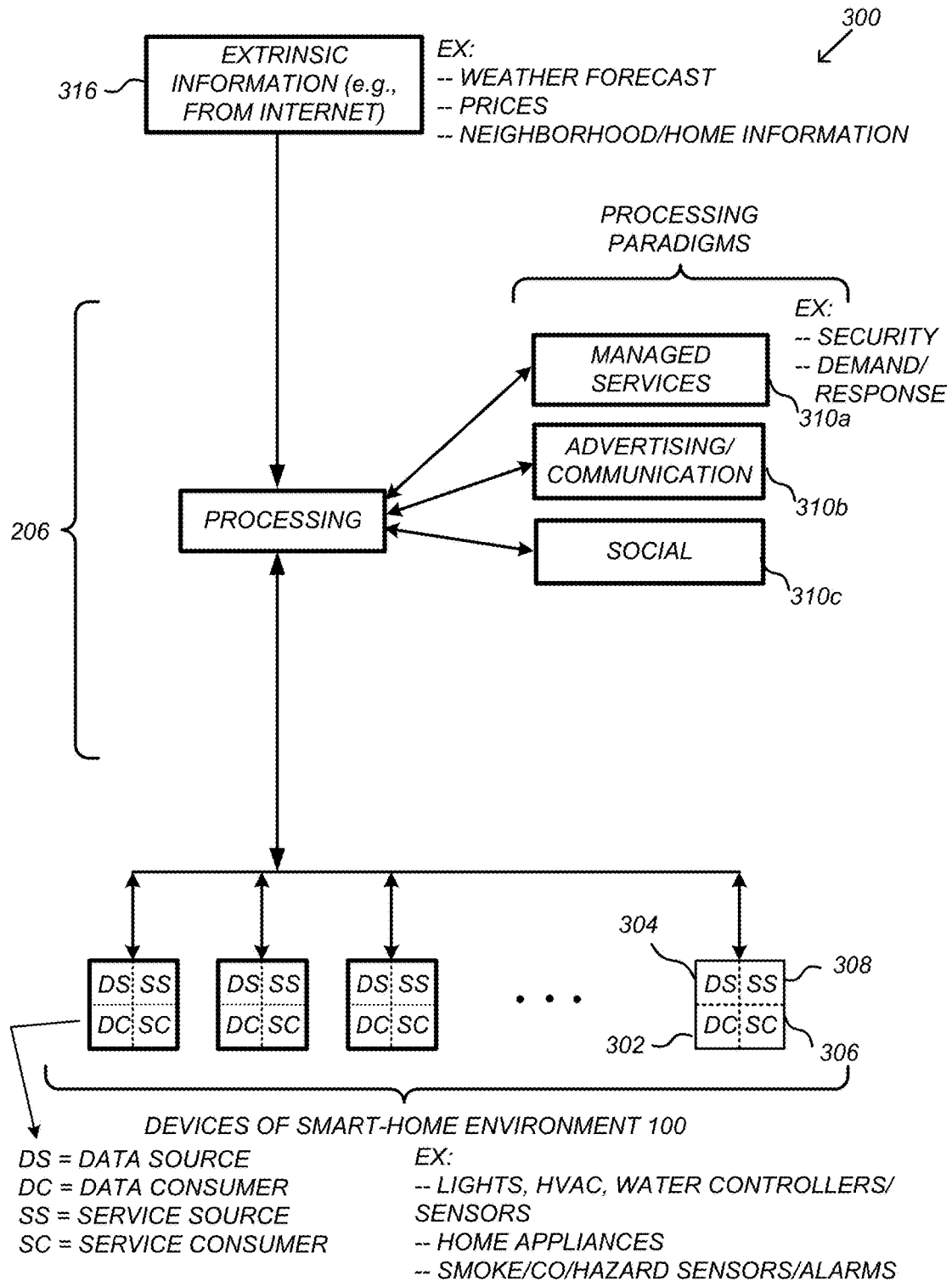
FIG. 3 is an abstracted functional view of one embodiment of a system for generating customized hazard notifications based on user activity.

FIG. 3 is an abstracted functional view of one embodiment of a system 300 for generating customized hazard notifications based on user activity. Smart devices, such as those of the smart-home environment 100 of FIG. 1, share common characteristics in that each smart device is a data consumer 302 (DC), a data source 304 (DS), a services consumer 306 (SC), and a services source 308 (SS). System 300 can be configured to harness the large amount of data generated by the smart devices to provide a variety of automated, extensible, flexible, and/or scalable technologies for achieving useful objectives. These objectives may be predefined or adaptively identified based on, e.g., user activity data or user input.

System 300 includes processing engine 206, which further includes a number of paradigms 310. Processing engine 206 can include a managed services paradigm 310a that monitors and manages device functions, such as ensuring proper operation of a device, responding to emergency situations, or detecting failure of equipment coupled to the device (e.g., a burned out light bulb). Processing engine 206 can further include an advertising/communication paradigm 310b that identifies characteristics (e.g., demographic information) of a user or products of interest to a user based on device usage. Processing engine 206 can further include a social paradigm 310c that collects data from and transmits data to a social network. For example, a user's status as reported on the social network can be collected and processed to determine user activity.

The processing engine 206 can also utilize extrinsic information 316 with the processing paradigms. Extrinsic information 316 can be used to interpret data received from a smart device, to determine a characteristic of the environment near the smart device (e.g., outside an enclosure that contains the smart device), to determine services or products available to the user, to identify a social network or social-network information, to determine contact information of entities (e.g., public service entities such as an emergency response team, the police or a hospital) near the smart device, or to identify statistical or environmental conditions, trends or other information associated with a home or neighborhood.

Figure 4:
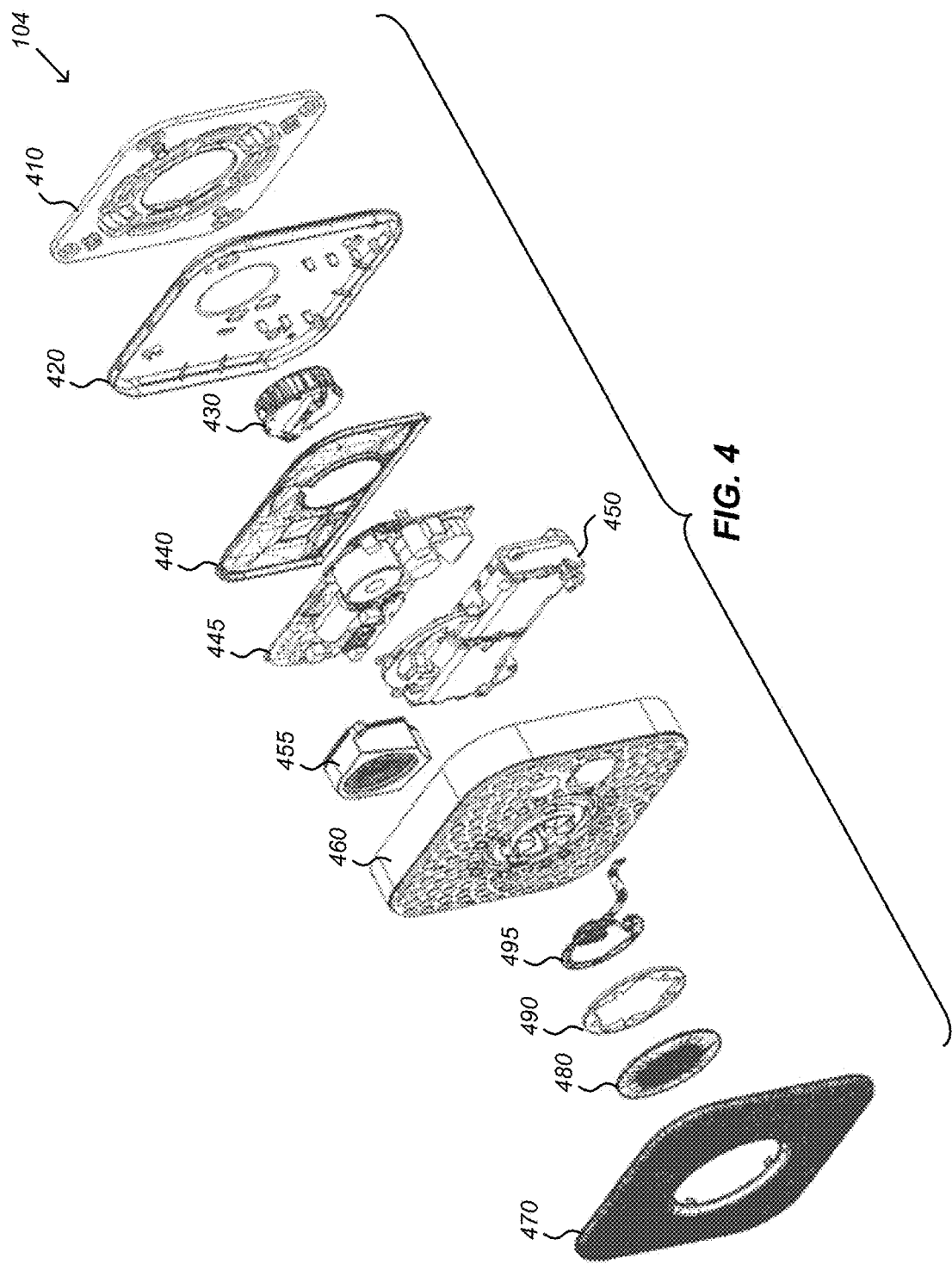
FIG. 4 is an illustration of an exploded perspective view of a smart hazard detector that is included in an embodiment of a system for generating customized hazard notifications based on user activity.

FIG. 4 is an illustration of an exploded perspective view of a smart hazard detector 104 that is included in an embodiment of a system for generating customized hazard notifications based on user activity. Hazard detector 104 can include a smoke detector, carbon monoxide detector, heat detector, and humidity sensor. Hazard detector 104 is configured to sound an audible notification, such as an alarm, when a sufficient level (e.g., above a threshold setting) of smoke or some other hazardous substance is detected. In one embodiment, hazard detector 104 also includes other sensors such as a motion sensor or ambient light sensor. Hazard detector 104 can also include a wireless transceiver for transmitting data, e.g., when a hazardous substance or user activity is detected, to other smart devices or a computer server system.

In one embodiment, hazard detector 104 is a roughly square or rectangular shaped object having a width of approximately 120 to 134 mm and a thickness of approximately 38 mm. Hazard detector 104 includes a mounting plate 410 that can be attached to a wall or ceiling and a back plate 420 that can be mounted to the mounting plate 410. Hazard detector 104 further includes a front casing 460 that can be secured to the back plate 420 to define a housing with an interior region for containing the components of the hazard detector 104.

A circuit board 445 can be attached to the back plate 420 and various components can be mounted to the circuit board 445. For example, a smoke chamber 430 can be mounted on circuit board 445 and configured to detect the presence of smoke. In one embodiment, smoke chamber 430 can be mid-mounted relative to circuit board 445 so that air can flow into smoke chamber 430 from above the circuit board 445 and below the circuit board 445. A speaker 455 and alarm device (not numbered) can also be mounted on circuit board 445 to audibly warn an occupant of a potential fire danger when the presence of smoke is detected in the smoke chamber 430. Other components, such as a motion sensor (e.g., ultrasonic, passive IR, etc.), carbon monoxide sensor, temperature sensor, heat sensor, ambient light sensor, noise sensor, microprocessor, and the like may likewise be mounted on circuit board 445.

In one embodiment, a protective plate 440 can be attached to circuit board 445 to provide a visually pleasing appearance to the inner components of hazard detector 104 or to funnel airflow to smoke chamber 430. For example, when a user views the internal components of hazard detector 104, such as through the vents in back plate 420, protective plate 440 can provide the appearance of a relatively smooth surface and otherwise hide the components or circuitry of circuit board 445. Protective plate 440 can likewise function to direct air flow from the vents of back plate 420 toward smoke chamber 430.

Hazard detector 104 can also include a battery pack 450, which can be the main source of power for the various components of hazard detector 104. In one embodiment, battery pack 450 is a backup power source and hazard detector 104 is further coupled with a primary external power source, such as a 120 V power source of the home or enclosure. In some embodiments, a cover plate 470 can be attached to the front casing 460 to provide a visually pleasing appearance or for other functional purposes. In a specific embodiment, cover plate 470 may include a plurality of holes or openings so that the sensors on circuit board 445 can detect external objects. The plurality of openings can be arranged to provide a visually pleasing appearance when viewed. For example, the openings can be arranged according to a repeating pattern, such as a Fibonacci or other sequence.

A lens button 480 can be coupled with or otherwise mounted to cover plate 470. Lens button 480 can be transparent, allowing the sensors to view through the lens button 480. For example, a PIR sensor (not shown) can be positioned behind the lens button 480 to detect the activity or movement of a user. In some embodiments, lens button 480 can also function as a pressable button for inputting commands, such as to shut off a false alarm. A light ring 490 can be positioned distally behind lens button 480. The light ring 490 can be configured to receive and disperse light, e.g., from an LED or other light source, so as to provide a desired visual appearance, such as a halo, behind the lens button 480. A flexible circuit board 495 that includes one or more electrical components, such as a PIR sensor or LEDs, can be positioned behind the light ring 490. Flexible circuit board 495 can be electrically coupled to circuit board 445, enabling data communications with one or more microprocessors mounted on circuit board 445.

Figure 5:
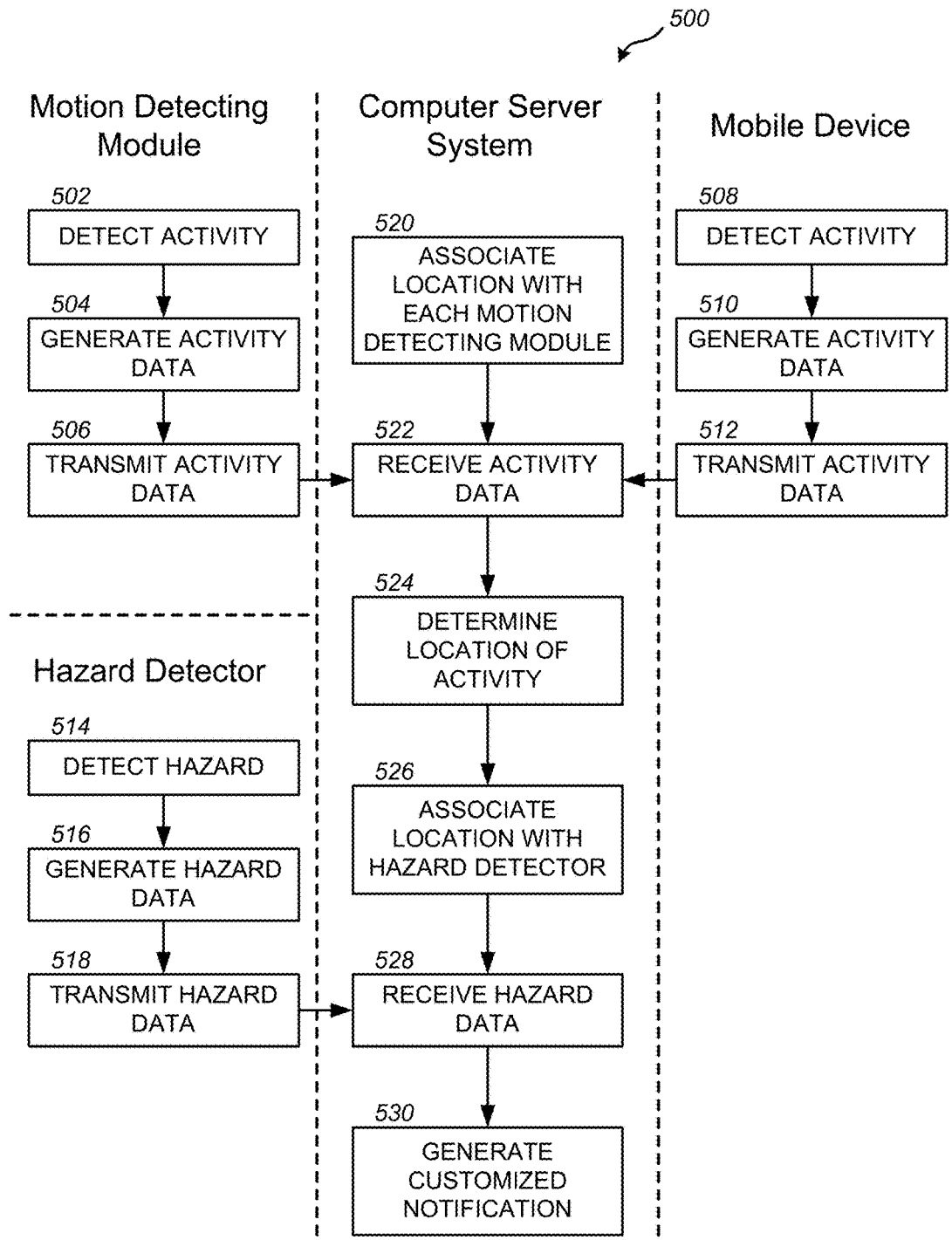
FIG. 5 is an interaction flowchart of one embodiment of a process for generating customized hazard notifications based on user activity.

FIG. 5 is an interaction flowchart of one embodiment of a process 500 for generating customized hazard notifications based on user activity. The flowchart illustrates the interactions between four components: a motion detecting module, a mobile device, a hazard detector, and a computer server system. The motion detecting module can be included as a part of any smart device, such as a smart hazard detector or a smart security camera. The motion detecting module includes a motion sensor (e.g., ultrasonic, PIR, or optical sensor), a processor for processing data from the motion sensor, and a network port or transceiver for transmitting data. The motion detecting module can also include other sensors to provide more detailed information regarding user activity. The mobile device can be a mobile phone or tablet of a user, or any other computing device of the user capable of detecting user activity and transmitting data. The hazard detector can be a smart hazard detector such as hazard detector 104 described herein above and illustrated in FIG. 4. The computer server system can include one or more computer servers, such as computer server system 164 described herein above with reference to FIG. 2.

In one embodiment, process 500 begins at block 502 when the motion detecting module detects user activity. User activity can be detected by a motion sensor, which is triggered if the user moves in front of the sensor. At block 504, the motion detecting module generates activity data indicating the detection of the user activity. The activity data can include a wide range of information related to user activity. In one embodiment, the activity data includes an indicator that the motion sensor was triggered and information identifying the motion detecting module or the smart device that includes the motion detecting module. In other embodiments, the activity data can further include information identifying the user (e.g., via facial recognition or RFID), information regarding the direction and extent of user movement, information regarding detected sounds during the user activity, and information from other sensors. At block 506, the activity data is transmitted to the computer server system.

In some embodiments, user activity data is collected from a mobile device of the user. At block 508, the mobile device detects user activity. The mobile device can include a multitude of sensors, such as global positioning system (GPS) sensors, acceleration sensors, and proximity sensors, any one of which can detect the user activity. User activity can also be detected with peripheral devices that are designed to work with mobile devices, such as an activity tracking wristband. At block 510, the mobile device, more specifically an application executed by the mobile device, generates activity data. The activity data can include location data, such as coordinates from the GPS, as well as data from other sensors or applications. For example, data can be gathered from third-party applications that communicate with the peripheral devices or from the peripheral devices directly using an API provided by the third-party, as discussed herein above with reference to FIG. 2. At block 512, the activity data is transmitted to the computer server system.

At block 514, the hazard detector is triggered by the presence of a hazardous substance. In one embodiment, the hazard detector is triggered if the level of hazardous substance present (i.e., the amount or concentration of the hazardous substance) is greater than a threshold setting. In other embodiments, the hazard detector can include multiple threshold settings for detecting different levels of the hazardous substance. At block 516, the hazard detector generates hazard data indicating the detection of the hazardous substance. The hazard data can include an identification of the hazard detector, as well as other information such as the level of the hazardous substance or data from other sensors in the hazard detector. At block 518, the hazard detector transmits the hazard data to the computer server system.

With reference now to the computer server system, at block 520, a location is associated with each motion detecting module. In one embodiment, the location is at a home or enclosure detail level, and specifies the room or location within the home or enclosure. In other embodiments, the location can specify coordinates, which can then be cross referenced with a map to determine a geographical location or location within the home or enclosure. The location can be provided by a user, e.g., when the smart device containing the motion detecting module is registered with an account, or the location can be provided by sensors, such as a GPS sensor. At block 522, user activity data is received from the motion detecting module or the mobile device. Although both sources are illustrated in this figure, the process 500 can be performed with just a single source of user activity data. User activity data from multiple sources can also be combined to provide more details regarding the activity. At block 524, a location of the activity is determined. If the activity data includes the location, the location can simply be extracted to determine the location. Otherwise, the identification of the motion detecting module or smart device can be used to determine the location that was associated with the module or smart device.

At block 526, the computer server system associates a location with the hazard detector. The location can be at a geographical level of detail, e.g., specify coordinates, or an enclosure level of detail, e.g., specify a room. The location can be provided by a user, e.g., when the hazard detector is registered with an account, or the location can be provided by sensors, such as a GPS sensor. At block 528, the hazard data is received from the hazard detector. In response to receiving the hazard data, a customized notification is generated at block 530. The notification is customized based on the user activity data that is received at block 522.

In one embodiment, the notification can be generated for an emergency response unit, such as a fire department or security/fire monitoring service, based on the user activity data. For example, a smart hazard detector or other smart device which include a motion or occupancy sensor can be placed in each room of an enclosure. If a hazardous situation is detected, a notification can be generated and transmitted to the fire department that indicates how many occupants there are in the enclosure and which rooms they are in.

In one embodiment, if the user activity data indicates that there are no users in the enclosure, the notification can be sent to the security/fire monitoring service, the user, or user specified emergency contacts. For example, the locations of the emergency contacts can also be collected and the distance between the enclosure and each user or contact is determined. The computer server system can then compare the distances to find the closest user or contact to notify. In another embodiment, the closest user or contact can receive a different notification than other users and contacts. Thus, the notification can vary depending on the distance between the user and the home. The notification can also indicate which rooms the hazardous substance is detected in. Thus, for example, if a user is coming home and smoke is detected in the garage, the notification can provide a warning to the user to not open the garage. User configurable settings can also be provided so that the user can specify what actions to take and which contacts to notify in different situations.

In other embodiments, the notification can be generated to provide exit directions for the user based on the user activity data. For example, a home account can be associated with user provided maps or maps can be generated from positional and other sensor information collected from smart devices in the home. When a hazardous situation is detected, activity data from motion sensors or GPS sensors can indicate which room the user is in. The notification can include exit routes from the user's location that avoid the hazard location. The notification can also instruct the user to go through the hazard location if necessary, and can provide advice on how to move through the hazard location to minimize exposure. The notification can be transmitted to the user's mobile device or to smart devices in the home that have speakers or displays. Smart devices with speakers can generate speech to communicate the exit directions to the user. Notifications can also be transmitted to smart devices along the exit route that have a light source so that lighting can be used to communicate the exit route to the user.

Figure 6:
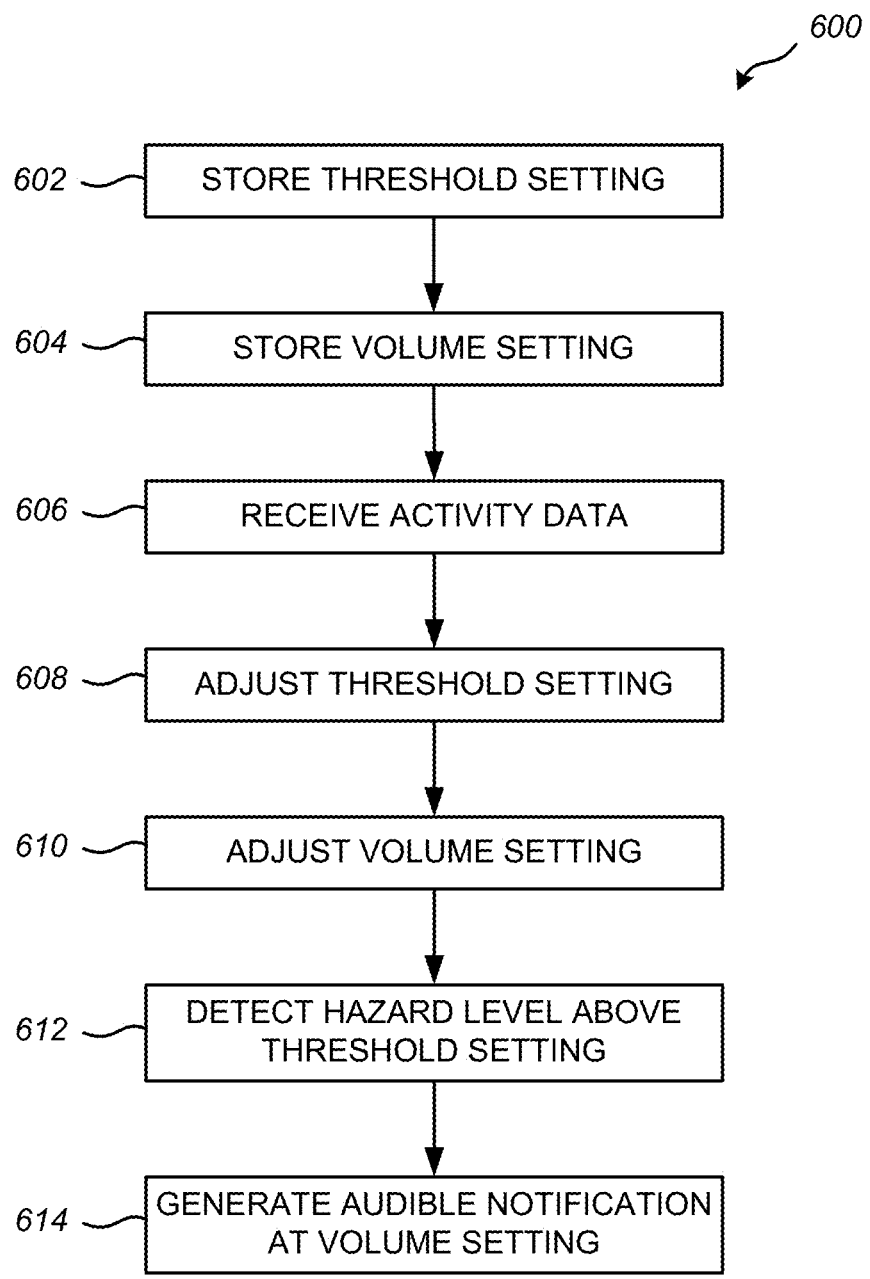
FIG. 6 is a flowchart of another embodiment of a process for generating customized hazard notifications based on user activity.

FIG. 6 is a flowchart of another embodiment of a process 600 for generating customized hazard notifications based on user activity. Process 600 starts at block 602, wherein a threshold setting is stored for a hazard detector. The threshold setting defines a level of hazardous substance at which an alarm or notification should be generated. In some embodiments, multiple threshold settings can be stored for the hazard detector, some corresponding to levels at which pre-alarms should be generated and some corresponding to levels at which an alarm should be generated. Different threshold settings can be stored for different hazardous substances. Some threshold settings can also be used to generate notifications indicating that the hazardous situation is improving. For example, if the level of hazardous substance decreases below a threshold setting, a notification can be generated that informs the user that the hazardous substance is clearing out. The threshold settings can be stored in a storage device within the hazard detector or with the computer server system.

At block 604, a volume setting is stored for the hazard detector. The volume setting specifies a volume level for audible alarms and notifications generated by the hazard detector, e.g., via a speaker or horn. In some embodiments, there can be multiple volume settings, one for each threshold setting or alarm/notification that the hazard detector generates. The volume settings can be stored with the hazard detector or with the computer server system.

At block 606, activity data is received indicating user activity. The activity data can be generated and received from smart devices in an enclosure or a mobile device of the user, as discussed herein above with reference to FIG. 5. At block 608, a threshold setting is adjusted based on the activity data, and at block 610, a volume setting is adjusted based on the activity data. In other embodiments, only one of the threshold setting or volume setting is adjusted based on the activity data. In one embodiment, the activity data is received by the computer server system and the computer server system performs the adjustments. In another embodiment, the activity data can be transmitted directly from the smart device that generated the activity data to the hazard detector via the mesh network, and the hazard detector can perform the adjustments.

In one embodiment, threshold or volume settings are adjusted when the activity data indicates that the user is asleep. Sensors in smart devices or mobile devices can generate activity data based on motion detection, facial recognition, or detected sound patterns that indicates the user is asleep. For example, if motion detectors did not detect the user leaving the room but no longer detects motion for a certain period of time, if facial recognition data indicates the user's eyes have been closed for a certain period of time, if sound patterns corresponding to snoring or other sleeping sounds are detected, or if no sound is detected for a certain period of time, it can be determined that the user is asleep. Other information can also be used to determine that the user is asleep. For example, room information associated with smart devices can indicate that the user stopped moving in a bedroom or other location that the user tends to sleep at (e.g., the living room, which can be determined from patterns in historical data). Ambient light sensors can indicate the user has turned off the lights. Some users also use sleep tracking applications or peripheral devices with their mobile device, the data of which can be collected using APIs to determine that the user is asleep. In one embodiment, if the user is determined to be asleep, a volume setting can be increased or a threshold setting can be decreased to provide a safer environment for the user.

In another embodiment, threshold or volume settings are adjusted when the activity data indicates that the user is cooking or taking a shower. Heat and humidity sensors in smart devices can detect that the temperature and humidity levels are rising in the kitchen or bathroom, and it can be determined that the user is cooking or showering. In response, a threshold setting for smoke can be increased since low levels of smoke will be due to the cooking or showering activity, not a genuine hazardous situation. In one embodiment, the volume setting is increased if the user is showering, or performing any other activity that makes it difficult to hear the notification or alarm generated by the hazard detector, which can be detected with noise sensors. The volume setting can also be adjusted based on the activity location, such that the volume is increased if the activity location is farther away from the hazard detector and decreased if the activity location is closer to the hazard detector.

In yet another embodiment, the threshold setting is decreased if activity data indicates that the user is exercising. Motion sensors can detect repeated movements in one location or area, which can be used to determine that the user is exercising. Additional data can be collected from exercise tracking applications or peripheral devices that are used with a mobile device. A user is more susceptible to CO exposure when exercising, thus a threshold setting can be decreased for CO so that the user is notified even if only low levels of CO are present. Smokers and babies are also more susceptible to CO exposure. Thus, in other embodiments, the CO threshold setting is decreased if activity data indicates that the user is a smoker or that there is a baby in the home. The activity data can be collected from sensors, health tracking applications, or inputted by the user.

At block 612, the hazard detector detects a level of hazardous substance that is above the adjusted threshold setting. In response to detecting the level of hazardous substance, an audible notification or alarm is generated by the hazard detector at block 614. The audible notification or alarm is generated at a volume level corresponding to the adjusted volume setting.

Figure 7:
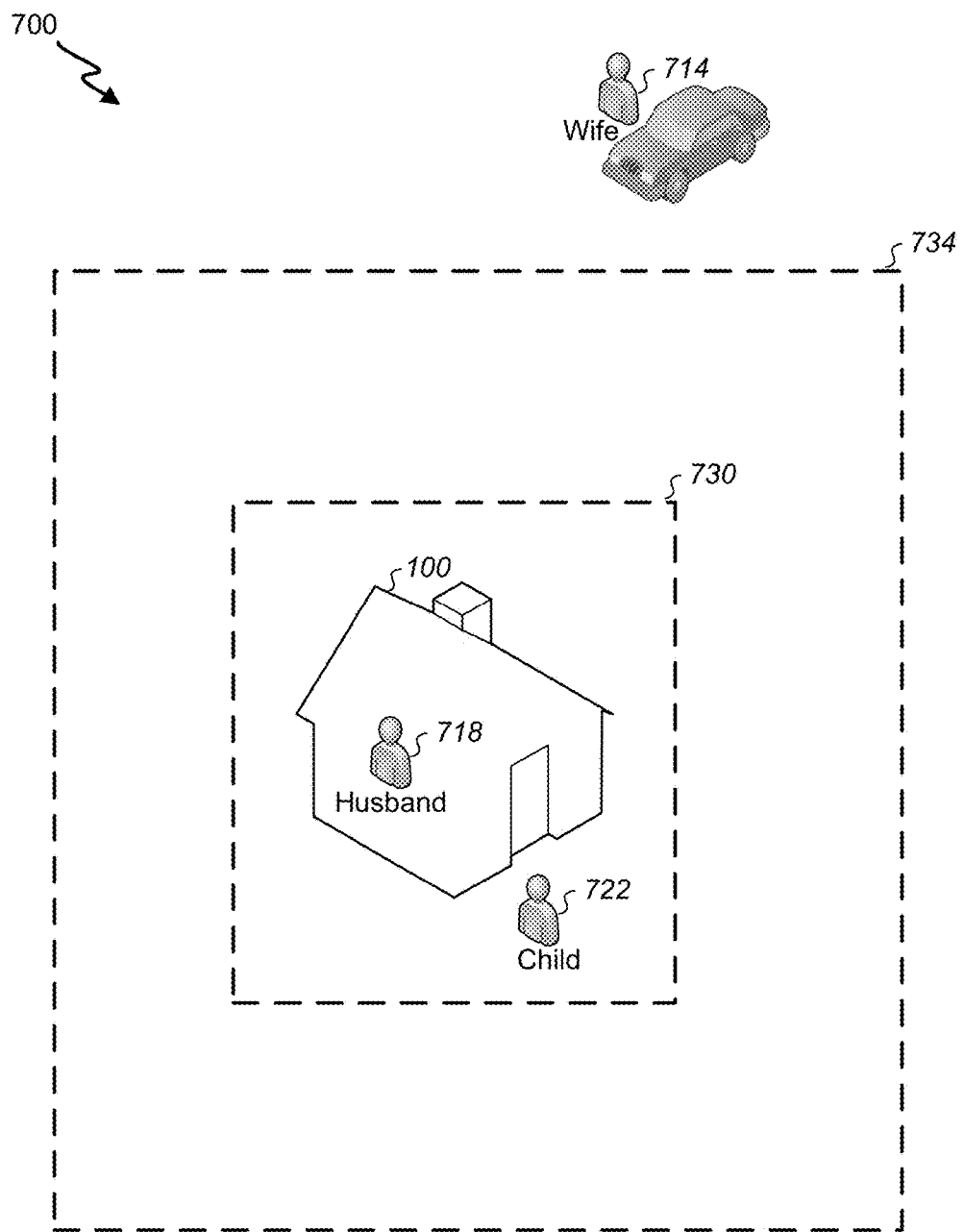
FIG. 7 is a schematic diagram of geo-fencing, which can be used in one embodiment of a system for generating customized hazard notifications based on user activity.

FIG. 7 is a schematic diagram of geo-fencing, which can be used in one embodiment of a system for generating customized hazard notifications based on user activity. When user activity data is received from the mobile device, and the location information is generated by GPS, it can be difficult to determine if the user is at the enclosure or away, depending on the accuracy of the GPS. One or more geo-fences can be established to assist the system with determining whether the user is at the enclosure or away in these instances. The geo-fences can also be used to determine if the user is leaving the enclosure or returning to the enclosure.

In the example illustrated in FIG. 7, the users include Wife 714, Husband 718 and Child 722, each of whom have registered their mobile device with the computer server system as being associated with the smart-home environment 100. Further, two geo-fences 730, 734 are associated with the smart-home environment 100. In some embodiments, the users define and register the geo-fences, while in other embodiments the computer server system generates the geo-fences for the home.

Inner geo-fence 730 defines the perimeter of living area of the home. The area within the inner-geo fence includes not only the home but also the land immediately surrounding the house, including any closely associated structures, such as garages or sheds ("the cartilage"). Outer geo-fence 734 defines an outer perimeter, which is sometimes miles from the home. The outer geo-fence 734 is adjustable and extends well beyond the curtilage. For example, the perimeter defined by the outer geo-fence 734 can have a radius of two to three miles in some embodiments, while in other embodiments the radius is larger or smaller.

According to embodiments, the computer server system determines that a user is at home when inside the inner geo-fence 730 and that the user is away when outside the inner geo-fence 730. Further, the computer server system determines that a user is going home when the user moves (e.g., travels by car) from outside to inside the outer geo-fence 734 and that the user is leaving home when the user moves from inside to outside the inner geo-fence 730. Therefore, the computer server system uses the inner geo-fence 730 to determine when users leave the home, and uses the outer geo-fence 734 to determine when users are returning home.

Figure 8:
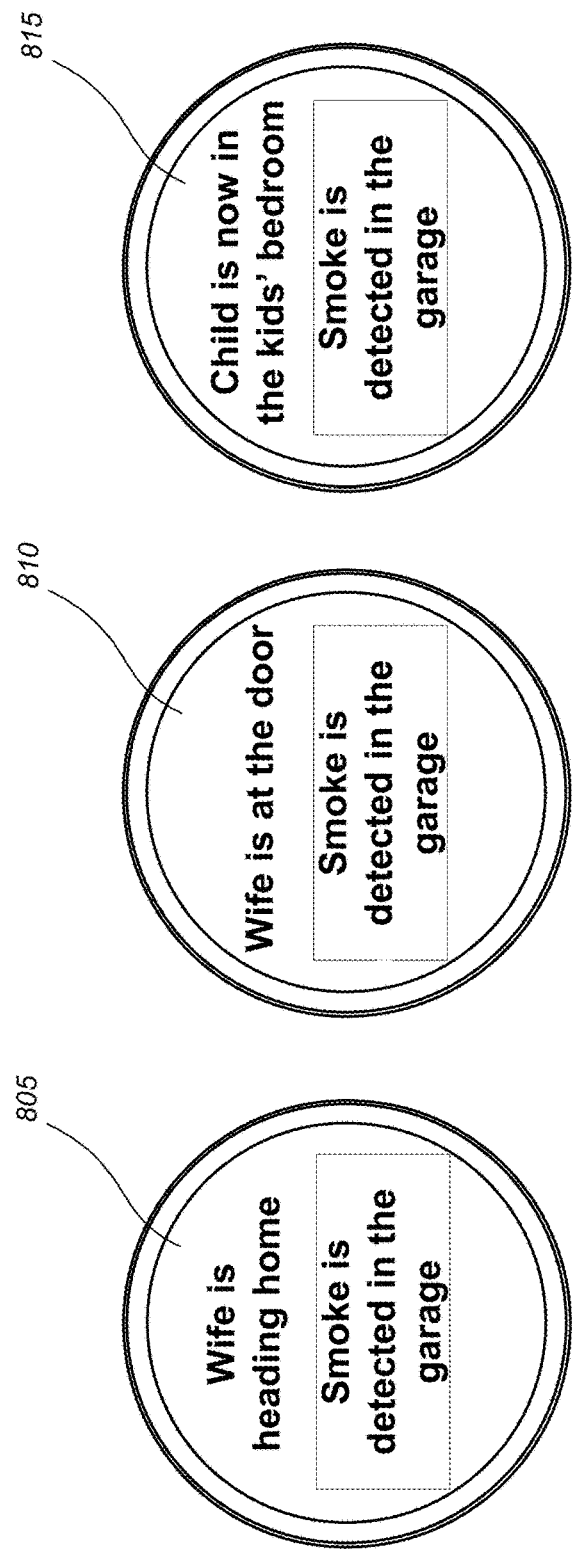
FIG. 8 is an illustration of exemplary customized notifications that can be displayed on smart devices in one embodiment of a system for generating customized hazard notifications based on user activity.

FIG. 8 is an illustration of exemplary customized notifications that can be displayed on smart devices in one embodiment of a system for generating customized hazard notifications based on user activity. For example, upon determining that Wife 714 is heading home, a corresponding notification can be transmitted to a smart device causing the smart device to display a message 805 that says, "Wife is heading home. Smoke is detected in the garage." Likewise, when it is determined that Wife 714 is leaving home, a corresponding message can be displayed. When Wife 714 arrives home and moves near the door, a corresponding notification can be transmitted to the smart device to display a message 810 that says, "Wife is at the door. Smoke is detected in the garage." This notification can be generated and transmitted when wife 714 moves close to or within inner geo-fence 730. In other embodiments, the notification is generated and transmitted when a smart device, such as the smart entryway device 106 depicted in FIG. 1, detects Wife 714 or communicates with the mobile device of Wife 714. In another example, upon detecting that Child 722 has moved to a different room of the home, a customized notification can be sent to the smart device to display a message 815 that says, "Child is now in the kids bedroom. Smoke is detected in the garage."

Alternatively or in conjunction with displaying a message, the smart device can also generate an audible speech notification. For example, while displaying message 805, a smart hazard detector can also generate the audible notification: "*beep *beep *beep Smoke is in the garage. *beep *beep *beep Wife is heading home." In another example, the smart hazard detector can generate the following audible notification while displaying message 810: "*beep *beep *beep Smoke is in the garage. *beep *beep *beep Wife is at the door." In a further example, the smart hazard detector can display message 815 while generating the audible notification: "*beep *beep *beep Smoke is in the garage. *beep *beep *beep Child is now in the kids' bedroom."

The customized notifications can be transmitted to any smart device, mobile device, or computing device when a hazardous situation is detected to provide a more effective emergency response. For example, a notification can be transmitted to a smart entryway device to display a message that indicates how many users are in the enclosure and what rooms they are in. This way, when an emergency response unit or emergency contact arrives at the enclosure, they have more information regarding the situation, which can be used to determine what actions to take and the priority of the each action.

Figure 9:
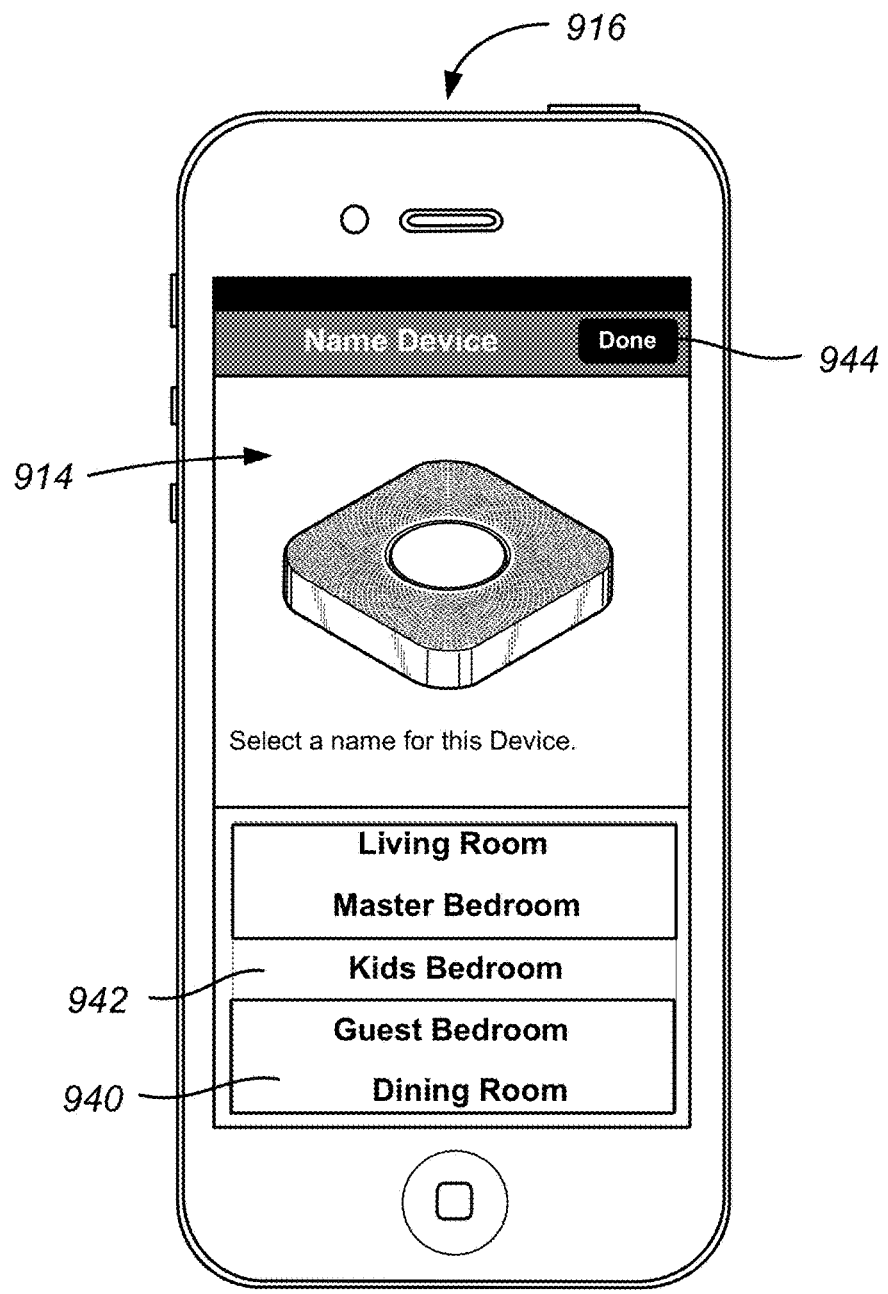
FIG. 9 is an illustration of an example method for associating locations with smart hazard detectors or other smart devices that can be used in one embodiment of a system for generating customized hazard notifications based on user activity.

FIG. 9 is an illustration of an example method for associating locations with smart hazard detectors or other smart devices that can be used in one embodiment of a system for generating customized hazard notifications based on user activity. During the device initialization or registration process, an interface can be provided to allow a user to select a room or location for the smart hazard detector or smart device that generates activity data. In this example, the interface is provided in an application 914 executed by a mobile device 916. The user can perform a slide gesture on a list object 940, causing the list of rooms to scroll up or down. This can be used to place one of the rooms in a select field 942. When the desired room appears in select field 942, the user can press the done button 944 to submit the room for association with the smart device. Alternatively, application 914 can simply provide a field for the user to enter a room or location that is to be associated with the smart device.

Figure 10:
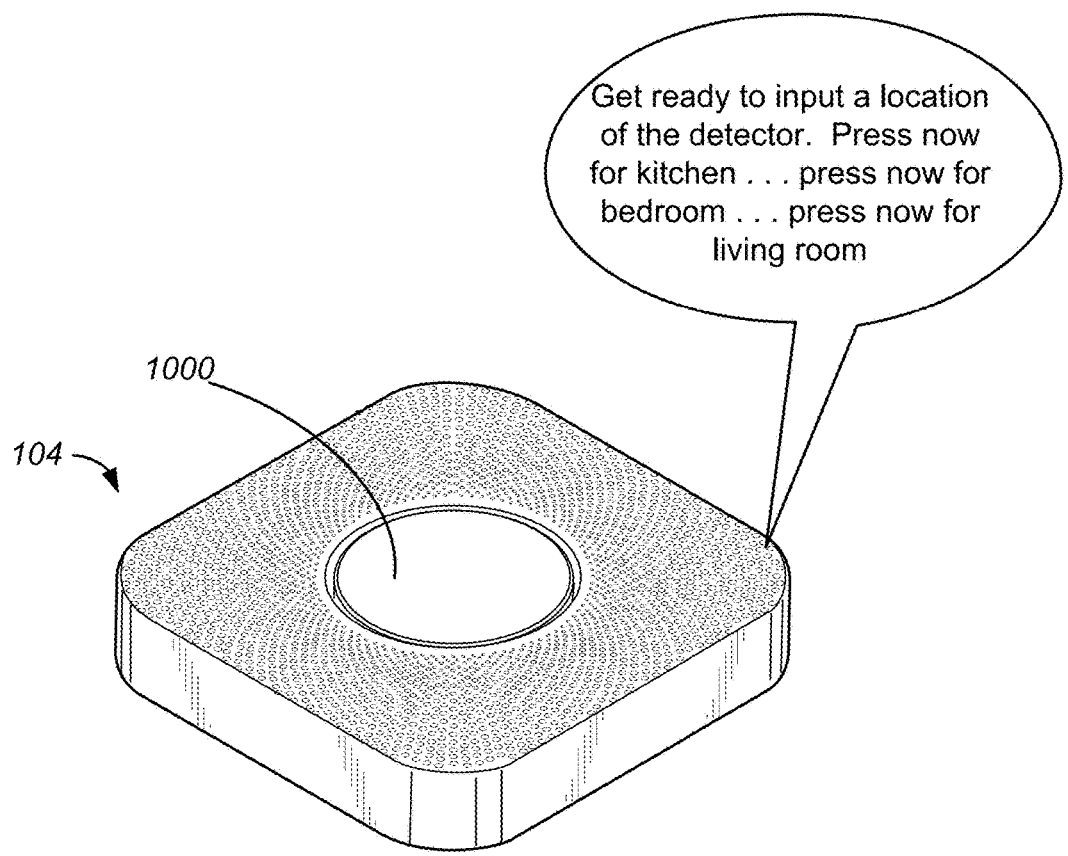
FIG. 10 is an illustration of another example method for associating locations with smart hazard detectors or other smart devices that can be used in one embodiment of a system for generating customized hazard notifications based on user activity.

FIG. 10 is an illustration of another example method for associating locations with smart hazard detectors or other smart devices that can be used in one embodiment of a system for generating customized hazard notifications based on user activity. In this example, the smart device is the smart hazard detector 104 illustrated in FIG. 1. However, this method can be used to associate a location with any smart device.

The hazard detector 104 generates audible instructions telling the user, "Get ready to input a location of the detector." The smart device pauses for a moment and then tells the user, "Press now for kitchen." If the user presses button 1000 soon after hearing the instruction, then the kitchen location is associated with hazard detector 104. If, however, the user does not press button 1000, hazard detector 104 tells the user, "Press now for bedroom." This process can continue until the user selects a location. It should be appreciated that these audible instructions are provided for illustrative purposes only, and any number of words and word combinations can be used to communicate the same instructions.

Figure 11:
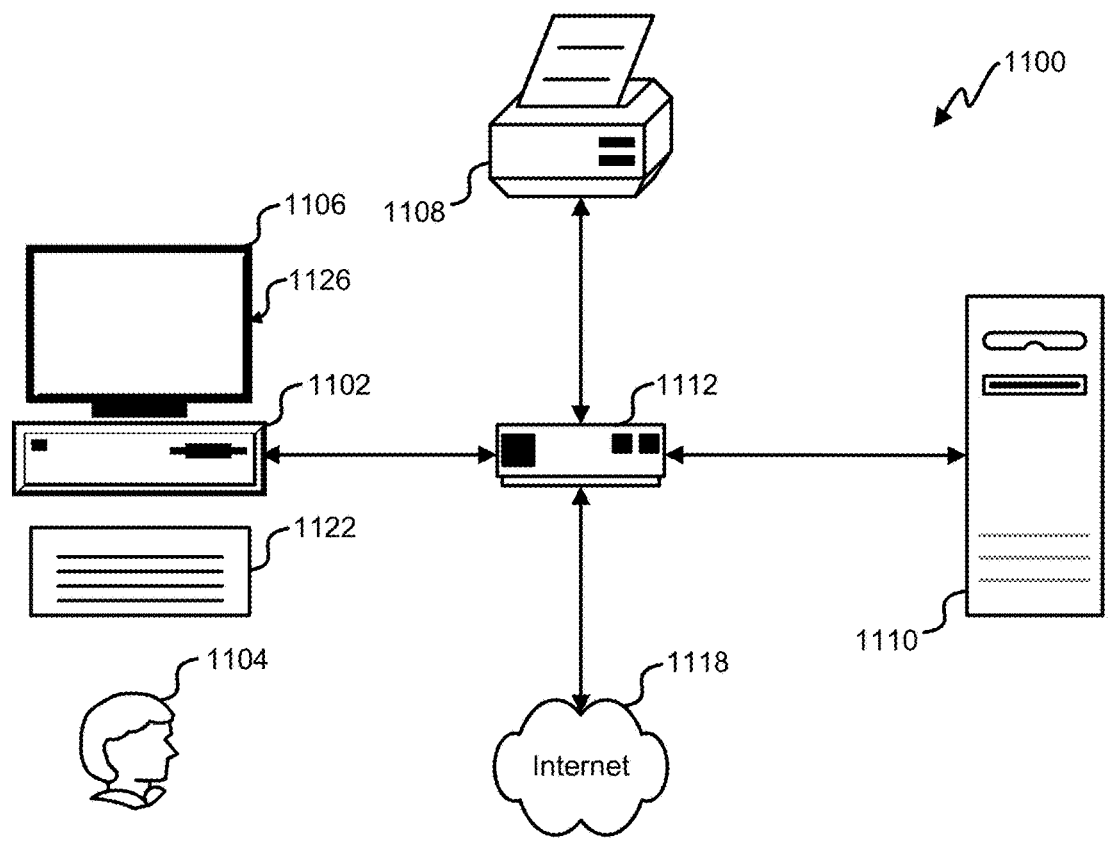
FIG. 11 is a block diagram of an exemplary environment for implementing one embodiment of a system for generating customized hazard notifications based on user activity.

FIG. 11 is a block diagram of an exemplary environment for implementing one embodiment of a system for generating customized hazard notifications based on user activity. The exemplary environment includes a computer system 1100 that can be used by a user 1104 to remotely control, for example, one or more of the smart devices according to one or more of the embodiments described herein. The computer system 1100 can alternatively be used for carrying out one or more of the server-based processing described herein above or as a processing device in a larger distributed computer server system for carrying out processing. The computer system 1100 can include a computer 1102, keyboard 1122, a network router 1112, a printer 1108, and a monitor 1106. The monitor 1106, processor 1102 and keyboard 1122 are part of a computer system 1126, which can be a laptop computer, desktop computer, handheld computer, mainframe computer, etc. The monitor 1106 can be a CRT, flat screen, etc.

A user 1104 can input commands into the computer 1102 using various input devices, such as a mouse, keyboard 1122, track ball, touch screen, etc. If the computer system 1100 comprises a mainframe, a designer 1104 can access the computer 1102 using, for example, a terminal or terminal interface. Additionally, the computer system 1126 may be connected to a printer 1108 and a server 1110 using a network router 1112, which may connect to the Internet 1118 or a WAN. While only one server 1110 is shown in the figure, it is understood that computer system 1126 can be connected to any number of servers.

The server 1110 may be used to store additional software programs and data. In one embodiment, software implementing the systems and methods described herein can be stored on a storage medium in the server 1110. Thus, the software can be run from the storage medium in the server 1110. In another embodiment, software implementing the systems and methods described herein can be stored on a storage medium in the computer 1102. Thus, the software can be run from the storage medium in the computer system 1126. Therefore, in this embodiment, the software can be used whether or not computer 1102 is connected to network router 1112. Printer 1108 may be connected directly to computer 1102, in which case, the computer system 1126 can print whether or not it is connected to network router 1112.

Figure 12:
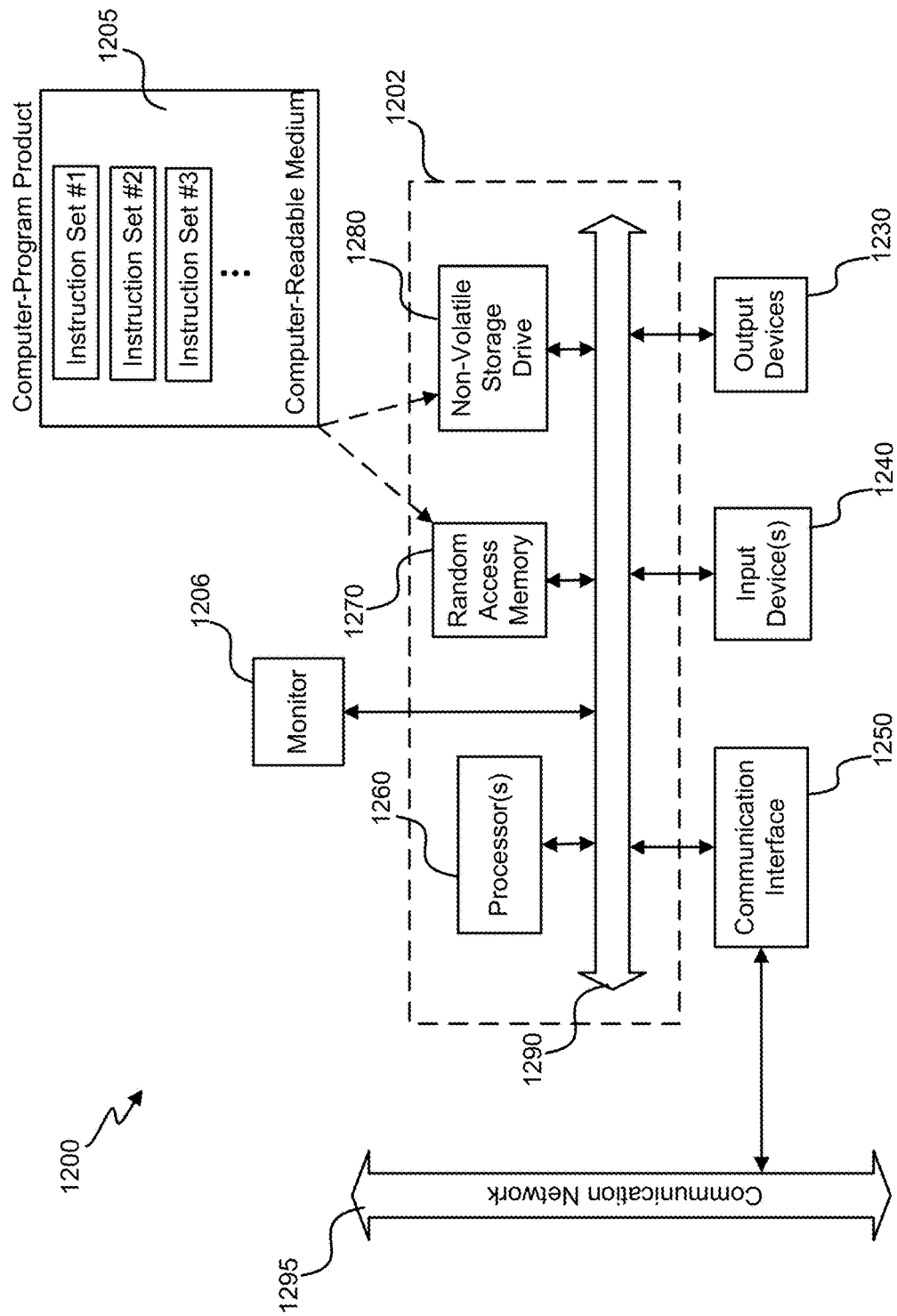
FIG. 12 is a block diagram of an embodiment of a special-purpose computer system for generating customized hazard notifications based on user activity.

FIG. 12 is a block diagram of an embodiment of a special-purpose computer system 1200 for generating customized hazard notifications based on user activity. The methods and systems described herein may be implemented by computer-program products that direct a computer system to perform the actions of the methods and components. Each such computer-program product may comprise sets of instructions (codes) embodied on a computer-readable medium that directs the processor of a computer system to perform corresponding actions. The instructions may be configured to run in sequential order, or in parallel (such as under different processing threads), or in a combination thereof.

Special-purpose computer system 1200 comprises a computer 1202, a monitor 1206 coupled to computer 1202, one or more additional user output devices 1230 (optional) coupled to computer 1202, one or more user input devices 1240 (e.g., keyboard, mouse, track ball, touch screen) coupled to computer 1202, an optional communications interface 1250 coupled to computer 1202, a computer-program product 1205 stored in a tangible computer-readable memory in computer 1202. Computer-program product 1205 directs system 1200 to perform the above-described methods. Computer 1202 may include one or more processors 1260 that communicate with a number of peripheral devices via a bus subsystem 1290. These peripheral devices may include user output device(s) 1230, user input device(s) 1240, communications interface 1250, and a storage subsystem, such as random access memory (RAM) 1270 and non-transitory storage drive 1280 (e.g., disk drive, optical drive, solid state drive), which are forms of tangible computer-readable memory.

Computer-program product 1205 may be stored in non-transitory storage drive 1280 or another computer-readable medium accessible to computer 1202 and loaded into memory 1270. Each processor 1260 may comprise a microprocessor, such as a microprocessor from Intel® or Advanced Micro Devices, Inc.®, or the like. To support computer-program product 1205, the computer 1202 runs an operating system that handles the communications of product 1205 with the above-noted components, as well as the communications between the above-noted components in support of the computer-program product 1205. Exemplary operating systems include Windows® or the like from Microsoft Corporation, Solaris® from Sun Microsystems, LINUX, UNIX, and the like.

User input devices 1240 include all possible types of devices and mechanisms to input information to computer system 1202. These may include a keyboard, a keypad, a mouse, a scanner, a digital drawing pad, a touch screen incorporated into the display, audio input devices such as voice recognition systems, microphones, and other types of input devices. In various embodiments, user input devices 1240 are typically embodied as a computer mouse, a trackball, a track pad, a joystick, wireless remote, a drawing tablet, a voice command system. User input devices 1240 typically allow a user to select objects, icons, text and the like that appear on the monitor 1206 via a command such as a click of a button or the like. User output devices 1230 include all possible types of devices and mechanisms to output information from computer 1202. These may include a display (e.g., monitor 1206), printers, non-visual displays such as audio output devices, etc.

Communications interface 1250 provides an interface to other communication networks and devices and may serve as an interface to receive data from and transmit data to other systems, WANs and/or the Internet 1118. Embodiments of communications interface 1250 typically include an Ethernet card, a modem (telephone, satellite, cable, ISDN), a (asynchronous) digital subscriber line (DSL) unit, a FireWire® interface, a USB® interface, a wireless network adapter, and the like. For example, communications interface 1250 may be coupled to a computer network, to a FireWire® bus, or the like. In other embodiments, communications interface 1250 may be physically integrated on the motherboard of computer 1202, and/or may be a software program, or the like.

RAM 1270 and non-transitory storage drive 1280 are examples of tangible computer-readable media configured to store data such as computer-program product embodiments of the present invention, including executable computer code, human-readable code, or the like. Other types of tangible computer-readable media include floppy disks, removable hard disks, optical storage media such as CD-ROMs, DVDs, bar codes, semiconductor memories such as flash memories, read-only-memories (ROMs), battery-backed volatile memories, networked storage devices, and the like. RAM 1270 and non-transitory storage drive 1280 may be configured to store the basic programming and data constructs that provide the functionality of various embodiments of the present invention, as described above.

Software instruction sets that provide the functionality of the present invention may be stored in RAM 1270 and non-transitory storage drive 1280. These instruction sets or code may be executed by the processor(s) 1260. RAM 1270 and non-transitory storage drive 1280 may also provide a repository to store data and data structures used in accordance with the present invention. RAM 1270 and non-transitory storage drive 1280 may include a number of memories including a main random access memory (RAM) to store instructions and data during program execution and a read-only memory (ROM) in which fixed instructions are stored. RAM 1270 and non-transitory storage drive 1280 may include a file storage subsystem providing persistent (non-transitory) storage of program and/or data files. RAM 1270 and non-transitory storage drive 1280 may also include removable storage systems, such as removable flash memory.

Bus subsystem 1290 provides a mechanism to allow the various components and subsystems of computer 1202 to communicate with each other as intended. Although bus subsystem 1290 is shown schematically as a single bus, alternative embodiments of the bus subsystem may utilize multiple busses or communication paths within the computer 1202.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system for customizing hazard notifications based on user activity, the system comprising:
    a plurality of motion detecting modules, each motion detecting module being configured to:
        detect activity based on one or more users moving,
        generate activity data indicating the detection of the activity, the activity data indicative of the one or more users moving, and
        transmit the activity data to a computer server system;
    a hazard detector configured to:
        detect a hazard level that is greater than a threshold setting, the hazard level indicating an amount of at least one of smoke and carbon monoxide (CO) present at the hazard detector,
        generate hazard data indicating the detection of the hazard level, and
        transmit the hazard data to the computer server system; and
    the computer server system being communicatively coupled to the plurality of motion detecting modules and the hazard detector, the computer server system being configured to:
        associate an activity location with each of the plurality of motion detecting modules, the activity location indicating a location of an associated motion detecting module within an enclosure,
        receive a first activity data indicative of the one or more users moving as detected by a motion detecting module of the plurality of motion detecting modules,
        identify a first motion detecting module that transmitted the first activity data,
        determine a first activity location associated with the first motion detecting module,
        receive the hazard data, and
        generate a hazard notification in response to receiving the hazard data, wherein the hazard notification indicates the first activity location and a hazard, and the first activity location is distinct from a location of the hazard.

2. The system of claim 1, wherein the hazard notification includes navigational directions for exiting the enclosure from the first activity location.

3. The system of claim 1, wherein the computer server system is further configured to transmit the hazard notification to the hazard detector, and wherein the hazard detector is further configured to communicate the hazard notification to a user.

4. The system of claim 3, wherein the hazard detector includes a light source, wherein the hazard detector communicates the hazard notification by activating the light source, and wherein the computer server system transmits the hazard notification to the hazard detector based on a location of the hazard detector within the enclosure.

5. The system of claim 3, wherein the hazard detector communicates the hazard notification via generated speech.

6. A method for customizing hazard notifications based on user activity, the method comprising:
    storing a threshold setting for a hazard detector;
    storing a volume setting for audio output of the hazard detector;
    receiving activity data indicating an activity of a user being performed distinct of the hazard detector;
    adjusting at least one of the threshold setting and the volume setting of the hazard detector based on the activity data;

detecting a hazard level that is greater than the threshold setting, the hazard level indicating an amount of at least one of smoke and carbon monoxide (CO) present at the hazard detector; and generating an audible notification in response to detecting the hazard level, the audible notification having a volume corresponding to the volume setting.

7. The method of claim 6, further comprising:
determining that the user is sleeping based on the activity data; and
increasing the volume setting based on determining that the user is sleeping.

8. The method of claim 6, further comprising:
determining that the user is exercising based on the activity data; and
decreasing the threshold setting based on determining that the user is exercising.

9. The method of claim 6, further comprising:
determining that the user is cooking based on the activity data; and
increasing the threshold setting based on determining that the user is cooking.

10. The method of claim 6, further comprising:
associating a hazard location with the hazard detector, the hazard location indicating a location of the hazard detector within an enclosure;
determining a distance between the hazard location and a user location, wherein the activity data further indicates the user location; and
adjusting the volume setting based on the distance.

11. A system for customizing hazard notifications based on user activity, the system comprising:
a hazard detector configured to:
detect a hazard level that is greater than a threshold setting, the hazard level indicating an amount of at least one of smoke and carbon monoxide (CO) present at the hazard detector,
generate hazard data indicating the detection of the hazard level, and
transmit the hazard data to a computer server system; and
the computer server system being communicatively coupled to the hazard detector and configured to:
associate a hazard location with the hazard detector, the hazard location indicating a location of the hazard detector,
receive activity data indicating a user location of a user and an identity of the user,
receive the hazard data, and
generate a notification in response to receiving the hazard data, the notification indicating the hazard location, the identity of the user and the user location.

12. The system of claim 11, further comprising:
a location module executed by a mobile device and configured to:
receive the user location from a global positioning system (GPS) of the mobile device,
generate the activity data indicating the user location, and
transmit the activity data to the computer server system.

13. The system of claim 11, wherein the hazard location is an enclosure location, the enclosure location indicating a location of an enclosure that contains the hazard detector.

14. The system of claim 13, wherein the computer server system is further configured to:
associate an inner geo-fence with the enclosure location, the inner geo-fence defining a perimeter around the enclosure, and
determine whether the user location is within the inner geo-fence.

15. The system of claim 14, wherein the computer server system is further configured to:
associate an outer geo-fence with the enclosure location, the outer geo-fence defining a perimeter around the enclosure that surrounds the inner geo-fence and is larger than the inner geo-fence,
receive a first activity data indicating the user location moved from outside the outer geo-fence to inside the outer geo-fence,
determine that the user is heading home based on the first activity data,
receive a second activity data indicating the user location moved from inside the inner geo-fence to outside the inner geo-fence, and
determine that the user is leaving home based on the second activity data,
wherein the notification is generated based on whether the user is heading home or leaving home.

16. The system of claim 11, wherein the computer server system is further configured to:
determine that the user is at the hazard location, and
transmit the notification to an emergency response unit based on determining that the user is at the hazard location.

17. The system of claim 11, wherein the computer server system is further configured to:
determine that the user is not at the hazard location, and
transmit the notification to an emergency contact based on determining that the user is not at the hazard location, the emergency contact being defined by the user.

18. The system of claim 17, wherein the computer server system is further configured to:
receive a contact location indicating a location of the emergency contact, and
determine a contact distance indicating a distance between the contact location and the hazard location,
wherein the notification is transmitted to the emergency contact further based on the contact distance.

19. The system of claim 18, wherein the computer server system is further configured to:
determine a user distance indicating a distance between the user location and the hazard location, and
compare the contact distance to the user distance.

20. The system of claim 11, wherein the notification includes an indication of whether the user is at the hazard location.

* * * * *